United States Patent [19]

Fang

[11] Patent Number: 5,474,893

[45] Date of Patent: Dec. 12, 1995

[54] SPECTROPHOTOMETRY OF AMYLOID DEGRADING ACTIVITY IN SERUM OR TISSUE

[76] Inventor: Ta-yun Fang, 13755 NW. Burton St., Portland, Oreg. 97229

[21] Appl. No.: 225,815

[22] Filed: Apr. 11, 1994

[51] Int. Cl.$^6$ .............................. C12Q 1/00; G01N 33/48
[52] U.S. Cl. ............................ 435/4; 435/7.21; 436/63; 436/164; 436/811
[58] Field of Search ..................... 435/4, 7.21; 436/63, 436/164, 811

[56] References Cited

U.S. PATENT DOCUMENTS

| | | | |
|---|---|---|---|
| 5,221,607 | 6/1993 | Cordell et al. | 436/811 |
| 5,276,059 | 1/1994 | Caughey | 514/647 |

FOREIGN PATENT DOCUMENTS

| | | |
|---|---|---|
| 2-55956 | 2/1990 | Japan . |
| 2218100A | 8/1989 | United Kingdom . |

OTHER PUBLICATIONS

Mata et al, *Chemical Abstracts*, vol. 113, p. 386, Ref. #94382c, 1990 (JP0255,956C9055,956).
Rao, *Chemical Abstracts*, vol. 93, p. 302, Ref.–#182229g, 1980 (Proc. Univ. Otago Med. Sch. 1980,58(2)57–58)
Elhaddoui et al, *Chemical Abstracts*, vol. 116, p. 377, Ref. #25138h, 1992 (J. Mol. Struct. 1992, 267, 113–116).
Glenner et al, *Biochem, Biophys. Res. Commun*,. vol. 120, No. 3, pp. 883–890, May 16, 1984.
"Demonstration of Amyloid–Degrading Activity in Normal Human Serum," by Igal Kedar (Keizman), Ezra Sohar, and Joseph Gafni (Introduced by M. Wolman); Proceedings of the Society for Experimental Biology and Medicine 145, 343–345 (1974).
"Degradation of amyloid by a serum component and inhibition of degradation," by Igal Kedar, Ezra Sohar, and Mordechai Ravid; J. Lab. Clin. Med, May 1982, vol. 99, No. 5; pp. 693–700.
"A Noninvasive Screening of Systemic Reactive (Secondary) AA Amyloidosis, Based on Reduced Amyloid Degrading Activity of Amyloidotic Serum," by Mordchai Ravid, Yona Greenman, Jeremia Shapira, and Igal Kedar; Israel J. Med, Sci., vol. 26, No. 4, Apr. 1990; pp. 191–194.
"Alzheimer's Disease: Initial Report of the Purification and Characterization of a Novel Cerebrovascular Amyloid Protein," by George G. Glenner, M.D. and Cainc W. Wong; Biochemical and Biophysical Research Communications, vol. 120, No. 3, 1984, May 16, 1984; pp. 885–890.
"The Characterization of Soluble Amyloid Prepared in Water," by M. Pras, M. Schubert, D. Zucker–Franklin, A. Rimon and E. C. Franklin; The Journal of Clinical Investigation, vol. 47, 1968, pp. 924–933.

*Primary Examiner*—Michael G. Wityshyn
*Assistant Examiner*—Abdel A. Mohamed
*Attorney, Agent, or Firm*—Klarquist Sparkman Campbell Leigh & Whinston

[57] ABSTRACT

A method for spectrophotometric measurement of amyloid degrading activity in serum or tissue is disclosed. The method involves first binding a dye to a purified amyloid protein. Preferably, the dye and the amyloid bind stably, yet reversibly, so that the bond is disrupted and the dye is released when the bound amyloid is degraded by amyloid degrading factors (ADF) present in serum or tissue. Preferably, the dye is Congo red. The composition comprising a dye bound to a purified amyloid protein is mixed with serum or tissue homogenate to form a reaction mixture. Degradation of the amyloid by ADF disrupts the dye/amyloid bond causing dye to be released into a supernatant solution where its concentration and amount are spectrophotometrically determined. The amount of the amyloid degraded is calculated based upon the quantity of the dye found in the supernatant.

20 Claims, 3 Drawing Sheets

SPECTROPHOTOMETRY OF AMYLOID DEGRADING ACTIVITY IN SERUM OR TISSUE

FIELD OF THE INVENTION

This invention concerns a spectrophotometric method for measuring amyloid degrading activity in serum or tissue. The method is useful in the early prognosis of amyloidosis and for investigation of amyloid metabolism.

BACKGROUND OF THE INVENTION

Reduced amyloid A degrading activity (ADA) in human serum has been found to correlate positively with a diagnosis of secondary amyloidosis. Ravid M., Greenman Y., Shapira J., Kedar I., *Israel Journal of Medical Sciences*, 26, 191–194 (1990); Wegelius O. Teppo Anna-M, Maury CPJ, *British Medical Journal*, 284, 617–619 (1982); Maury CP, Teppo Anna-M, *The Lancet*, July, 234–237 (1982).

Amyloid A is one member of a heterogenous group of proteins known generally as amyloids which share certain characteristics, including the binding of sodium diphenyl-diazo-bis-alpha-naphthylamine sulfonate (Congo red) and the consequent exhibition of green birefringence under polarized light; a β-pleated sheet structure as revealed by x-ray diffraction; and a fibrillar appearance with periodic twists when examined under the electron microscope.

Amyloidosis is a collective name for a number of diverse diseases having as a common feature the extra-cellular deposition of an amyloid protein onto affected tissues. This amyloid deposition appears to result from: 1) a reduction in amyloid degrading activity, a proteolytic activity that may be attributable to one or more specific amyloid degrading factors (ADF) present in serum and certain tissues and/or 2) increased synthesis of amyloid precursor proteins. Kedar I, Sohar E, Ravid M, *Journal of Laboratory and Clinical Medicine*, 99:693–700 (1982); Teppo A-M, Maury CPJ, Wegelius O. *Scand.J.Immunol.*, 16, 309–314 (1982); Shirahama T., Muira K., Ju S-T, Kisilevsky R., Gruys E., and Cohen A. S., "Amyloid Enhancing Factor-Loaded Macrophages in Amyloid Fibril Formation." *Laboratory Investigation* 62:61–68, 1990.

The amyloidoses are subdivided into the following disease categories based upon clinical manifestations and the nature of the precursor protein:

(1) Primary Amyloidosis: Although not associated with known disorders, it is most likely associated with plasma cell dysfunction, as in the case of multiple myeloma. For those patients, the amyloid protein involved is derived from impaired metabolism of immunoglobulin light chains, especially from immunoglobulin λ and K.

(2) Secondary Amyloidosis: Within this class of amyloidosis, extra-cellular deposition of amyloid A protein in organs is often the result of chronic inflammation and/or infection accompanying diseases such as rheumatoid arthritis, familial Mediterranean fever, myeloma, and neoplastic disorders. Circulating serum amyloid A (SAA) is the precursor of AA based on amino acid sequence homology and on immunological cross-reactivity.

(3) Alzheimer's Disease: Alzheimer's patients have intracerebral amyloid deposits in brain parenchyma occurring as intraneuronal neurofibrillary tangles, extracellular plaques and cerebrovascular amyloid deposits. The deposit is a 4KD protein known as βA4 or AβP (hereinafter AβP) which derives from an amyloid precursor protein.

(4) Endocrine-related Amyloidosis: Amyloid deposits are localized in the endocrine organs and/or specific cell groups of the endocrine gland. The amyloid protein deposited in these organs and/or cells often includes a polypeptide sequence homologous or identical to a portion of the polypeptide chain from related hormones, such as amylin found in the islets of Langerhan in Type II diabetes, or procalcitonin found in medullary carcinoma of the thyroid.

(5) Other Amyloidotic Diseases: (a) Systemic Amyloidosis results from regular, long-term hemodialysis treatment. The amino acid structure of the amyloid deposit in these patients is homologous to that of $\beta_2$-microglobulin; and (b) Senile-Related Amyloidosis, an amyloidotic condition in which an amyloid protein originating from prealbumin is deposited in the heart, aorta and other vessels. Patients suffering from familial polyneuropathy are also affected by an amyloid protein derived from prealbumin.

Secondary amyloidosis is known to affect many animals, including human and non-human primates, dogs, cats, bovines, golden hamsters, birds, snakes and honeybees. At present, accurate clinical diagnosis of secondary amyloidosis requires biopsy of abdominal fat, rectal tissue, or renal tissue, wherein the excised tissue is examined for amyloid A deposits. The tissue biopsy involves a painful surgical operation and carries the risks inherent to any invasive procedure. As a result, diagnosis of secondary amyloidosis in human patients frequently occurs at the later stages of the disease when organ enlargement is palpable and when the involvement of affected organs is extensive. At that stage of the disease, amyloid A infiltration is often irreversible, and death due to organ dysfunction can result.

ADA has been measured with agarose gel diffusion methods such as those described by Kedar I, Sohar E, Ravid M, *Journal of Laboratory and Clinical Medicine*, 99, 693–700 (1982) and Maury CPJ, Teppo A-M, Salaspuro MP, *Clinical Chimica Acta*, 131, 29–37 (1983). Briefly, the methods of Sohar and Maury involved first isolating and purifying a quantity of amyloid A protein. The purified amyloid A is incorporated into an agarose solution which is then poured into a Petri dish or onto a glass plate to form an opaque gel. Sample serum is allowed to diffuse into the gel through wells, followed by a room temperature incubation for 16 to 24 hours. ADA is indicated by the development of a clear, transparent zone adjacent to the wells. The approximate level of ADA is estimated by measuring the diameter of the cleared area.

SUMMARY OF THE INVENTION

The present invention is designed to enable earlier and more accurate prognosis of amyloidosis in primates, including human patients and other animals, than is possible with existing methods. The invention employs spectrophotometry to yield precise, quantitative measurement of amyloid degrading activity serum or tissue, reduced levels of which have been found to correlate positively with a diagnosis of amyloidosis in human patients.

The method of the present invention is practiced by following the steps of: (1) forming a composition comprising a quantity of dye bound to an amyloid; (2) adding to the composition a quantity of serum or tissue homogenate, thereby forming a reaction mixture; (3) incubating the reaction mixture; (4) spectrophotometrically measuring the quantity of dye present in the supernatant following incubation; and (5) calculating the quantity of the amyloid degraded based upon the quantity of dye found to be present in the supernatant. Preferably, the dye bound to the amyloid protein is Congo red. The structural conformation of Congo red is particularly suited to binding β-pleated sheet amyloid proteins, having long been used as a specific stain for the detection and/or quantification of amyloid proteins, including the amyloid A and AβP proteins. T. Kitamoto, et al. "A New Method to Classify Amyloid Fibril Proteins." *Acta Neuropathol* 67:272–278, 1985; G. G. Glenner, et al. "Alzheimer's Disease: Initial Report of the Purification and Characterization of a Novel Cerebrovascular Amyloid Protein. *Biochem. and Biophys. Res. Comm.* 120:885–890, 1984.

Preferably, the dye/amyloid composition is suspended in a buffer solution before addition of serum or tissue homogenate to initiate amylid degrading activity. More preferably, the Congo red/amyloid (CR-PA) composition is suspended in a phosphate buffered saline solution of pH between 6.0 and 10.0. Most preferably, the CR-PA is suspended in a phosphate buffered saline solution with a pH of about 6.8. It is further preferred that the serum or tissue homogenate be diluted before addition to the composition to form the reaction mixture.

Preferably, the resulting reaction mixture is incubated at from 35 to 40 degrees Celsius for between 20 and 60 minutes. More preferably, the reaction mixture is incubated at 37 degrees Celsius for about 30 minutes. Amyloid degrading activity is thought to result from the proteolytic activity of one or more ADF in serum and certain tissues. Thus, the CR-PA of the method is believed to serve as a substrate for amyloid degradation by the ADF.

Preferably, an aqueous NaCl solution is added to the mixture following the incubating and before spectrophotometrically measuring the quantity of dye present in the supernatant. This addition of aqueous NaCl facilitates precipitation of unreacted CR-PA, leaving free Congo red (or other dye) suspended in the supernatant for spectrophotometric measurement. More preferably, the final concentration of the NaCl in the reaction mixture is from about 0.5% to about 2.0% NaCl. Most preferably, the NaCl solution is about 0.9% NaCl.

Preferably, the step of spectrophotometrically measuring the amount of dye present in the supernatant is carried out with light at a wavelength in the range of from 450 nm to 550 nm. More preferably, the wavelength is about 505 nm. It is presumed that any quantities of unbound dye found in the supernatant are present because the dye/amyloid bond has been disrupted by chemical or physical alterations in the amyloid protein resulting from amyloid degrading activity.

After spectrophotometrically determining the amount of dye in the supernatant, the quantity of amyloid degraded can be calculated based upon the proportions in which the dye and amyloid bind. Amyloid degrading activity can be calculated in terms of milligrams of amyloid degraded per milliliter of serum or tissue homogenate added, or in terms of other suitable measurement units.

The amyloid degrading activity assay of the invention can be used alone, or in conjunction with other known assays, to diagnose the early onset of amyloidosis in primates, including human patients, and in other animals. For example, the method of the invention can be used in conjunction with existing SAA assays to diagnose secondary amyloidosis in human patients.

The present invention has a number of advantages over the existing agarose gel diffusion methods for measuring ADA, in particular, including but not limited to the following:

(1) The measurement of the cleared area on agar can be subjective, compromising the reliability of the assay. In contrast, spectrophotometric ADA measurement yields objective, precise results;

(2) The existing method requires an amyloid A sample size of at least from two to twelve times that required by the method of the invention. This is significant since amyloid A is not readily available commercially and is both costly and time consuming to prepare. Further, the gel diffusion methods result in the loss of unreacted amyloid A in the gel. In the method of the invention, unreacted amyloid A can be easily recovered for use in future assays;

(3) With the existing method, ADA depends upon diffusion of the serum through the amyloid A containing agar. If, as is thought, ADA is an enzymatic reaction, factors affecting enzymatic reactions such as substrate concentration, product inhibition, pH, ion concentration, etc. are difficult to control in a gel medium. Furthermore, incorporation of the amyloid A evenly into the agarose solution can only be achieved over a narrow temperature range, since agarose solution gels readily upon cooling while amyloid A protein denatures if overheated. With the method of the present invention, on the other hand, the ADA reaction proceeds in an aqueous medium where chemical and physical conditions are favorable for enzymatic reactions and relatively easy to control;

(4) With the existing method, the gel diffusion process takes 16 to 24 hours. In contrast, the ADA assay of the present invention requires only 20 to 30 minutes of incubation time; and (5) The method of the invention can be adapted for use in conjunction with other available assays for prognosis of secondary amyloidosis. The method of the present invention can also be used as a research tool for studying amyloid A metabolism and exploring potential therapies for secondary amyloidosis. On the other hand, the existing gel diffusion assay for ADA is difficult to combine with other available assays, and it is impractical to analyze the reaction products, impairing the utility of the existing ADA assay for research purposes.

Amyloid degrading activity appears to play an important role in the amyloid deposition and organ dysfunction characteristic of amyloidotic diseases. Yet, long after discovery of the connection between amyloid deposition and amyloidotic conditions such as secondary amyloidosis and Alzheimer's Disease, little is known about the synthesis and degradation of the amyloids associated with those diseases. Lack of progress in this area is due, in part, to the absence of a standardized, reliable assay to measure amyloid degrading activity. In particular, existing ADA gel diffusion methods are too slow and unreliable for wide-spread use as diagnostic assays for secondary amyloidosis in clinical laboratories. This fact has hampered the ability of physicians to determine which patients with chronic inflammatory diseases are at risk for developing secondary amyloidosis and are, therefore, candidates for therapeutic intervention.

The present invention can be formulated into a simple, fast and accurate amyloid degrading activity assay well-suited for use in both clinical and research laboratories. The invention will facilitate early prognosis and treatment of human patients and other animals at risk of developing progressive amyloidosis, and will help to further scientific understanding of the metabolism of amyloid proteins.

DETAILED DESCRIPTION OF THE INVENTION

Figure 1:
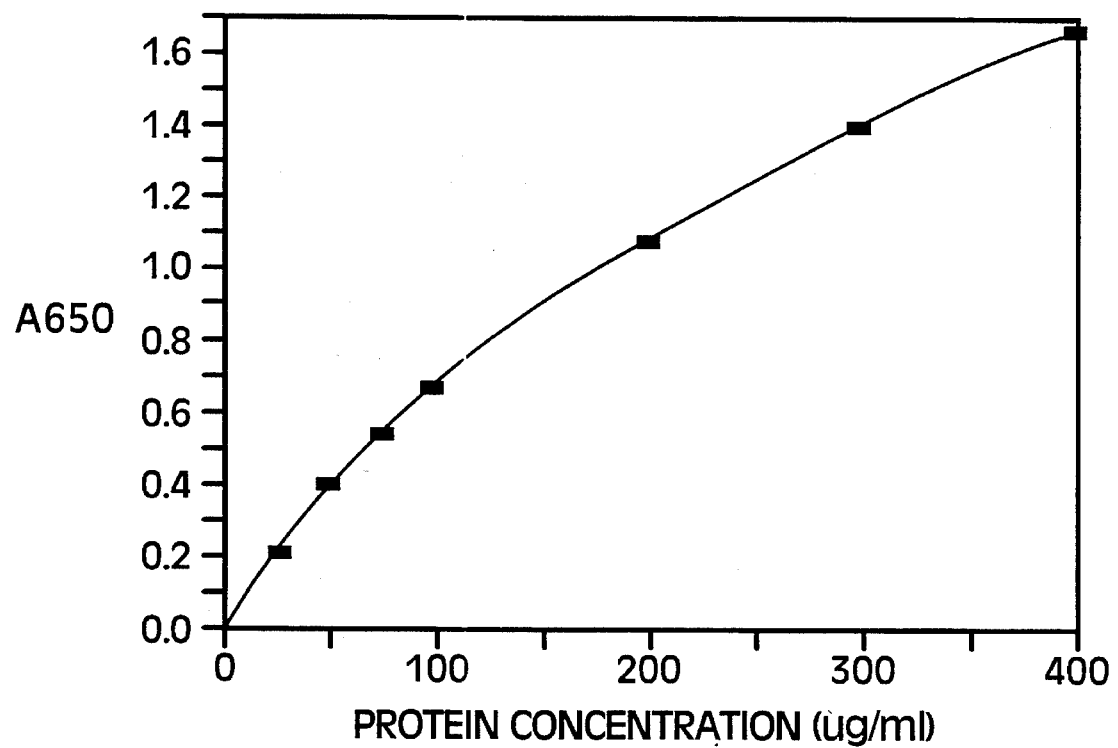
FIG. 1 is a graph showing the linear relation between spectrophotometric absorption at 650 nm and amyloid A concentration in the range of from 0 to 400 µg.

The present invention provides a method for spectrophotometrically measuring amyloid degrading activity in serum or tissue. The method of the invention comprises the steps of: (1) forming a composition comprising a quantity of a dye bound to an amyloid; (2) adding to the composition a quantity of serum or tissue homogenate, thereby forming a reaction mixture; (3) incubating the reaction mixture; (4) spectrophotometrically measuring the quantity of dye present in the supernatant following incubation; and (5) calculating the quantity of the amyloid degraded. The method of the present invention will enable earlier and more accurate prognosis of amyloidosis in primates, including human patients, and other animals, than is possible with existing diagnostic methods. The method of the invention will also facilitate scientific investigation of amyloid involvement in amyloidotic pathogenesis by providing an objective and quantitative assay for amyloid degrading activity.

Amyloid A can be obtained from human spleen tissue affected by primary amyloidosis as described in Pras, et. al., *The Journal of Clinical Investigation*, 47, 924–933 (1968). The Pras method can be used to isolate and purify amyloid proteins from a range of amyloidotic organ tissues taken from primates, including humans, and other animals.

A suitable approach for the present invention would be to follow the procedures described by Pras, et al. with some modifications to isolate and purify amyloid A from amyloidotic monkey liver tissue. The purity of the amyloid A preparation can be determined by procedures well-known in the chemical and biochemical literature, including Congo red staining, electron microscopic examination, SDS-PAGE/Western blot, immuno dot-blot, two dimensional gel electrophoresis, or radial immunodiffusion against anti-amyloid A antibody.

The amyloid β protein (AβP) associated with Alzheimer's Disease can be isolated and purified from human or monkey brains by using the method described in G. G. Glenner, et al. "Alzheimer's Disease: Initial Report of the Purification and Characterization of a Novel Cerebrovascular Amyloid Protein." *Biochem. and Biophys. Res. Comm.* 120:885–890, 1984.

After isolation and purification, a suitable dye is bound to the purified amyloid protein. A suitable dye is one that binds stably, yet reversibly to the amyloid. By reversibly bound, it is meant that degradation of an amyloid by ADF will disrupt the dye-protein bond so that the dye is released from the degraded protein into a supernatant. Preferably, the dye and the amyloid bind in constant proportions, as measured by weight, so that the quantity of dye found in the supernatant following amyloid degradation provides a reliable basis for calculating the quantity of amyloid degraded.

Most preferably, the dye is Congo red. Congo red is a classic dye used to stain cellulose. It is a linear molecule of tetrazotized benzidine coupled with two molecules of sodium naphthionate. The structural conformation of Congo red is especially suited to binding amyloid proteins, including amyloid A and AβP. For that reason, Congo red is widely used by those skilled in the art as a specific stain for the identification and measurement of amyloids generally. Congo red binds to amyloid A to form a composition which is from about 0.1 to about 0.45 mg dye per 1 mg protein as in Pras, Zucker-Franklin, Rimon, Franklin, *The Journal of Experimental Medicine*, 130, 777–791 (1969). More specifically, Congo red binds to amyloid A at a ratio of approximately 0.4 mg Congo red to 1.0 mg amyloid A.

A preferred method for binding Congo red to an amyloid involves first preparing two dilute solutions, one of Congo red and the other of a purified amyloid protein. A suitable Congo red solution can be prepared by dissolving Congo red in water, saline, or saline-containing ethanol. Preferably, a quantity of Congo red is dissolved in a solution of 0.9% NaCl in deionized water, resulting in a solution that is about 1% Congo red.

A suitable amyloid solution can be prepared by suspending a quantity of the purified amyloid in a dilute NaCl solution. Preferably, one mg/ml of a purified amyloid is suspended in a 0.9% NaCl solution. The concentration of the amyloid in the dilute NaCl solution can be determined by a modified version of the Lowry's protein assay described in Petersen GL, *Analytical Biochemistry*, 83, 346–356 (1977).

More specifically, the modified Lowry's protein assay involves first preparing a reagent (called "Reagent A"), comprising equal volumes of three solutions, those being: (1) copper/tartrate/carbonate (0.1%/0.2%/10); (2) 10% Sodium dodecyl sulfate (SDS); and (3) 0.8N NaOH in water. Next, the purified amyloid samples are diluted with deionized water. Then, equal volumes of Reagent A and the diluted amyloid solution are combined and allowed to react for a period of time. Preferably, the Reagent A/amyloid mixture is allowed to react at room temperature for about 10 minutes. After allowing the foregoing reaction to proceed for a sufficient time, a quantity of Folin-Ciocalteu phenol reagent is added and the resulting mixture is allowed to react for a period of time. Preferably, that mixture is allowed to react for at least 30 minutes. Finally, amyloid concentration is determined by spectrophotometrically measuring the absorbance of the final mixture and comparing that absorbance with a standard curve of known concentrations of bovine serum albumin (BSA). Preferably, within two hours from the end of the last reaction, the spectrophotometric absorbance of the mixture is measured at about 650 nm. A linear relation of absorbance at 650 nm to amyloid A protein concentrations ranging from 0 to 400 µg/ml is found. This relationship is demonstrated in FIG. 1.

Following the preparation of dilute solutions of Congo red and amyloid as described above, equal quantities of the two solutions are mixed together and incubated for a period of time. Preferably, the combined solutions are incubated for about one hour at room temperature with constant shaking. After incubation, Congo red stained amyloid (CR-PA) is collected by centrifugation. Preferably, the CR-PA is centrifuged at about 17,000×g for from 10 to 15 minutes. Preferably, the pellet is then restained with an equal amount of Congo red solution to ensure complete staining. The resulting CR-PA pellet is washed with saline and centrifuged. Preferably, the CR-PA pellet is washed three or more times with saline followed each time by centrifugation, such that after the final wash the spectrophotometric absorbance of the supernatant at 490 nm is less than 0.01.

After the CR-PA composition is formed according to the above procedures, serum or tissue homogenate is added and the ensuing amyloid degrading activity, if any, is quantitatively measured using spectrophotometric methods. A suitable method involves first suspending the CR-PA pellet in a dilute buffer solution. Preferably, the pellet is suspended in a dilute phosphate buffered saline (PBS) solution. Phosphate buffer (PB) is well known in the chemical and biochemical literature. It can be prepared by dissolving a quantity of phosphate monobasic and dibasic salts in deionized water and adjusting the pH to from about 6.0 to about 9.0. PBS is prepared from PB by adding a 0.9% NaCl solution to PB. Most preferably, the CR-PA pellet is suspended in a 0.01M PBS solution with a pH of about 6.8.

Next, a suitable quantity of diluted sample serum or tissue homogenate is added into the CR-PA suspension to initiate amyloid degrading activity, and the resulting reaction mixture is allowed to incubate at a suitable incubation temperature. Preferably, 1:10 diluted sample serum is added to the CR-PA suspension, and the reaction mixture is allowed to incubate for from 20 to 60 minutes at from 35 to 40 degrees Celsius. More preferably, the reaction mixture is allowed to incubate for 60 minutes at 37° C. Following incubation, the reaction mixture is adjusted to a 0.9% concentration by addition of a sodium chloride solution. Preferably, the solution is 9% NaCl. Next, a first supernatant is separated from unreacted CR-PA by centrifugation and the resulting CR-PA pellet is washed with PBS. After PBS washing, a second supernatant is formed by centrifugation, and the first and second supernatants are combined.

Figure 2:
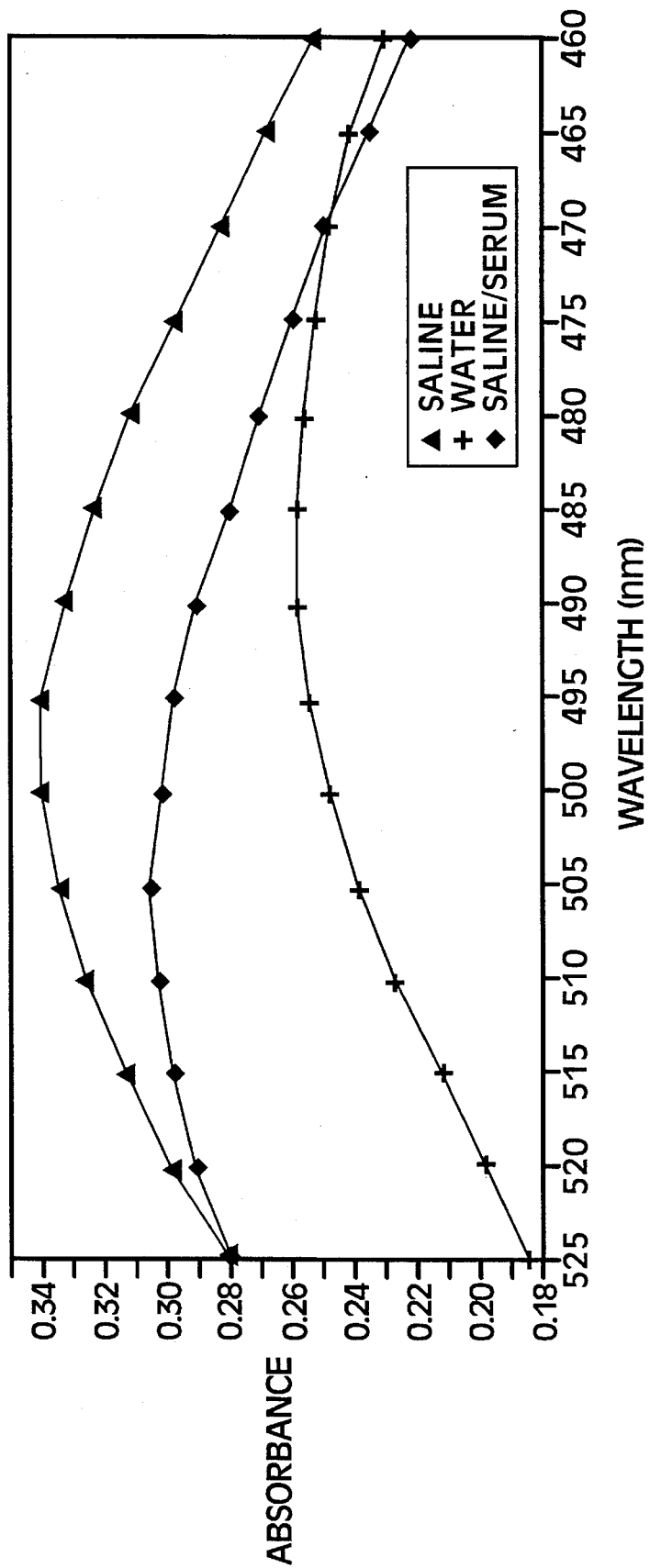
FIG. 2 is a graph showing the shift in peak spectrophotometric absorption of a Congo red/water solution in the presence of NaCl or bovine serum albumin (BSA).

Finally, the spectrophotometric absorption of the combined supernatants is measured. Preferably, the absorption of the combined supernatants is measured with light at a wavelength ranging from 450 nm to 550 nm. Most preferably, absorption is measured at about 505 nm, the peak absorption wavelength for a Congo red/serum solution. However, it should be noted that a shift of peak absorption is observed in the presence of NaCl or a protein such as bovine serum albumin (BSA). This shift is shown in FIG. 2.

Figure 3:
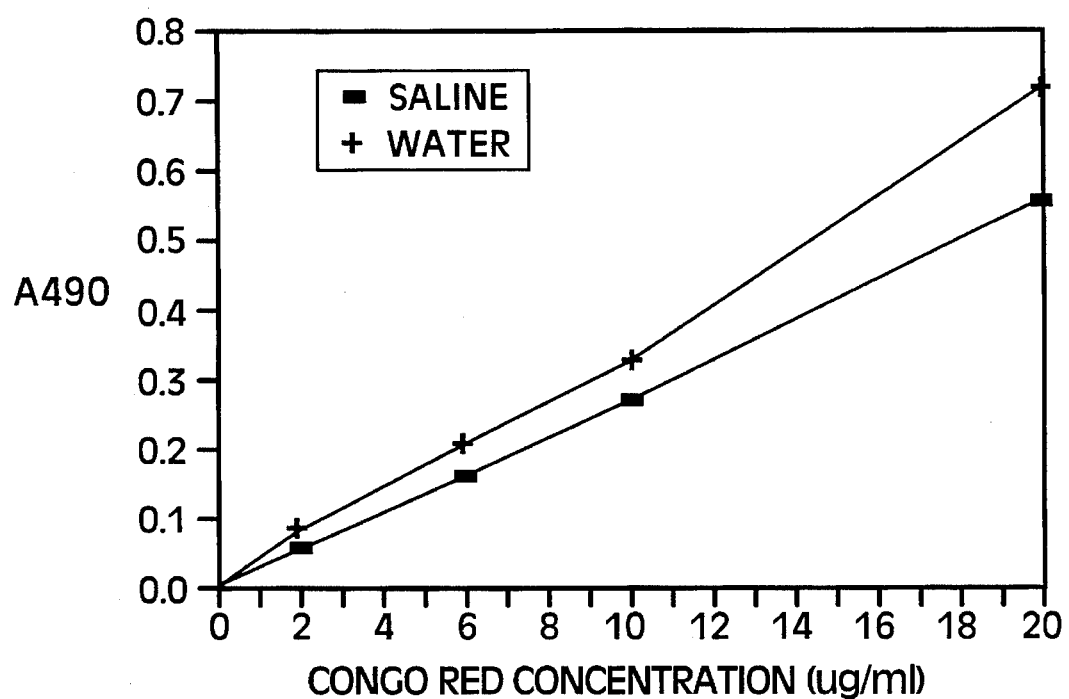
FIG. 3 is a graph showing the linear increase of spectrophotometric absorption at 490 nm for Congo red concentrations ranging from 0 to 20 µg/ml.

The amount of Congo red in the combined supernatants is determined by comparing the absorption curve of the supernatants with a standard curve for known concentrations of Congo red/saline solution. A linear absorption increase at 505 nm is observed for Congo red concentrations ranging from 0 to 20 µg per ml as shown in FIG. 3.

The quantity of the amyloid degraded per unit of serum or tissue homogenate can be calculated as a proportion of the quantity of Congo red found in the supernatant.

The invention will be further clarified by a consideration of the following examples, which are intended to be purely exemplary of the use of the invention.

EXAMPLE 1

Amyloid A was prepared in the laboratory from amyloidotic monkey liver tissue. The tissue was obtained from the Oregon Regional Primate Research Center, Beaverton, Oreg., and kept frozen until use. The amyloidotic condition of the monkey liver tissue was confirmed by microscopic examination after staining with Congo red.

The amyloidotic tissue was homogenized in 0.9% NaCl and centrifuged at 17,000×g for 30 minutes to remove soluble proteins. This process was repeated eight times, after which time the soluble protein content of the supernatant as measured by absorption at 280 nm was less than 0.2. The pellet was homogenized in 9% NaCl solution and centrifuged at 17,000×g for 30 minutes. The pellet was then re-homogenized in 0.9% NaCl and centrifuged at 17,000×g for 30 minutes.

Amyloid A was extracted from the resulting pellet by homogenization with deionized water followed by centrifugation at 17,000×g for 60 minutes. That process was repeated six times. The supernatants from the second to the sixth centrifugations were combined. Dissolved amyloid A was precipitated by adding 0.9% NaCl to the combined supernatants and incubating overnight at 4° C. Amyloid A was extracted from the resulting pellet by homogenization and centrifugation at 10,000×g for 15 minutes. The process of homogenization and centrifugation was repeated six times. Extracts numbers two through six were combined.

At intervals in the above process, the purity of the amyloid A preparation was determined with light microscopic examination after Congo red staining, SDS-PAGE, immuno dot-blot and radial immunodiffusion against anti-amyloid A antibody.

EXAMPLE 2

Congo red was bound to purified amyloid A using the following procedures:

One gram of Congo red was dissolved in a 0.9% aqueous NaCl solution and filtered. The concentration of Congo red after filtration was adjusted to 1 mg/ml according to the standard absorption curve of un-filtered aqueous Congo red solution at 490 nm.

One mg/ml purified amyloid A was suspended in 0.9% NaCl and the protein concentration was determined using a modified Lowry's assay, as described in Example 4 below. Equal volumes of the amyloid A and Congo red solutions were mixed and incubated for one hour at room temperature with continuous shaking. After incubating, Congo red stained amyloid A (CR-AA) was collected by centrifugation at 17,000×g for 10 minutes. The pellet was restained with an equal amount of Congo red solution to ensure complete staining. The resulting CR-AA pellet was washed three times with saline. After the third wash, the spectrophotometric absorbance of the supernatant at 490 nm read at less than 0.01. A modified Lowry's assay (Example 4) showed that the ratio of Congo red to amyloid A in CR-AA was about 0.4 mg of Congo red to about 1 mg of amyloid A.

EXAMPLE 3

The procedure according to Example 2 where the 1% Congo red solution to be reacted with the amyloid A solution is prepared by dissolving 1 gm of Congo red in one of the following: 0.9% NaCl in 80% ethanol; 0.9% NaCl in 80% ethanol made to 1% NaOH; or 0.9% NaCl in 50% ethanol.

EXAMPLE 4

A modified Lowry's protein assay was used to determine the amount of protein in tissue preparations, amyloid fractions and in reaction mixtures. First, a reagent (hereinafter "Reagent A") was prepared by mixing three solutions. Those solutions were prepared as follows:

| Solution 1: | Copper/tartrate/carbonate: | |
|---|---|---|
| | $CuSO_4$: | 100 mg |
| | Na, K tartrate: | 200 mg |
| | $Na_2CO_3$: | 10 gm |
| Solution 2: | Sodium dodecyl sulfate (SDS): | 10 gm |
| Solution 3: | .8 N NaOH: | 3.2 gm |

The above three solutions were each brought up to a final volume of 100 ml in deionized water and mixed in a 1:1:1 ratio to form Reagent A.

After preparing Reagent A, samples containing 10–100 μg of amyloid A were brought up to one ml with deionized water. One ml of Reagent A was added into the sample solution and reacted at room temperature. After 10 minutes, 0.5 ml of the Folin-Ciocalteu phenol reagent was added and the mixture was allowed to react for slightly more than 30 minutes. Within two hours, spectrophotometric absorbance at 650 nm was measured. The amount of protein in the sample was calculated by comparing sample absorbance at 650 nm with a standard curve of known concentrations of BSA at 650 nm.

EXAMPLE 5

ADA was measured by spectrophotometrically determining the quantity of Congo red released from CR-AA into a supernatant following incubation of CR-AA with a test serum. First, a phosphate buffered saline solution (PBS) was prepared as follows: (1) phosphate buffer was formed by preparing (A) 0.2M monobasic sodium phosphate (27.8 g/l) and (B) 0.2M dibasic sodium phosphate (53.65 g/l) stock solutions in deionized Concentration and pH were adjusted to 0.01M and 6.8 respectively by mixing 51 ml A with 49 ml B and diluting to 2 liters total volume with water; and (2) 9 gm NaCl was dissolved in 100 ml deionized water, and the resulting 9% saline solution was added to the phosphate buffer to form phosphate buffered saline (PBS) solution.

After PBS had been prepared, 75 μg CR-AA was pelleted by centrifugation at 10,000×g for 15 minutes and then suspended in 0.5 ml of 0.01M PBS. Twenty μl of 1:10 diluted sample serum was added into the CR-AA suspension to initiate ADA. The serum/CR-AA reaction mixture was then incubated at 37° C. for about 60 minutes. Next, 55 μl of 9% NaCl was added into the reaction mixture and mixed well. After centrifuging, the CR-AA pellet and a first supernatant were separated. The CR-AA pellet was washed with PBS and centrifuged, producing a second supernatant. The first and second supernatants were combined.

The spectrophotometric absorbance of the combined supernatants was measured at 505 nm and compared with the standard curves of known concentrations of Congo red/saline solution at 490 nm. From that comparison, the quantity of Congo red present in the supernatant fraction was determined. The quantity of amyloid A degraded was calculated in terms of mg/ml of serum based on the quantity of Congo red present in the supernatant.

EXAMPLE 6

The procedure according to Example 5 where the 100 μg of CR-AA is suspended in 0.01M phosphate buffer at pH 6.8.

EXAMPLE 7

ADA in tissue was measured by homogenizing crude monkey liver tissue and centrifuging at 10,000×g for sixty minutes, producing a first supernatant (S1). The pH of S1 was adjusted to 5.3 and centrifuged at 12,000×g for 30 minutes, producing S2. S2 was neutralized and centrifuged at 12,000×g for 15 minutes, producing S3. S3 was centrifuged at 12,000×g for 30 minutes, producing S4. S4 was centrifuged at 12,000×g for one hour, producing S5.

The S1 through S5 fractions were each separately added to the CR-AA/PBS suspension of Example 5 in place of the 1:10 diluted sample serum. The remaining steps of Example 5 were followed as before. The highest level of ADA per μg of amyloid A was found in the S5 fraction.

EXAMPLE 8

AβP can be isolated from human brains which are obtained from autopsy of former Alzheimer's patients and frozen at −70° C. Histological sections are taken and stained for amyloid. Sections with extensive cerebrovascular amyloidoses are selected for amyloid isolation. Non-amyloidotic tissues are removed from the selected histological sections and the remaining amyloidotic tissue is homogenized in 0.09% NaCl. Centrifugation at 12,500×g for 60 minutes at 4° C. results in a supernatant and a pellet with two visually distinct layers. The supernatant is discarded. The bi-layer pellet is frozen and an amyloid-enriched top brownish layer is dissected from a lower layer and saved. Repeated homogenization and centrifugation produces additional bi-layered pellets from which amyloid-enriched top brownish layers are dissected and combined with previous top-layer fractions.

The combined amyloid-enriched top layer fractions are homogenized in Tris-HCl buffer (0.05M, pH 7.5, containing $0.01M\ CaCl_2$ and 3 mM $NAN_3$) and made into a 4% solution (w/v). Type I collagenase is added into the homogenate in solid form at a 1:100 ratio. The digestion is allowed to proceed for eight hours at 37° C. The digestion product is collected by centrifuging at 105,000×g for 60 minutes at 4° C.

The pellet is further treated by adding 6M guanidine-HCl, 0.1M Tris-HCl, 25 mM dithiothreitol and 0.34 mM EDTA (pH 8.0) and stirring at room temperature for 48 hours. The insoluble pellet is separated by centrifugation at 105,000×g for 60 min. at 4° C. The resulting supernatant contains isolated AβP which is further purified by dialyzing in 1,000 molecular weight cut-off dialysis tubing and then lyophilizing.

The purified AβP is used for spectrophotometric measurement of AβP degrading activity in serum or tissue samples using the methods described in Examples 2 through 5 above.

EXAMPLE 9

The present invention can be developed into a clinical assay and used along with other available assays for an earlier and more accurate diagnosis of secondary amyloidosis than is possible with existing methods. Conversely, a negative ADA test obtained by the method of the present invention will obviate the need to biopsy tissue from a patient being screened for secondary amyloidosis. The invention has both medical and veterinary diagnostic utility.

Having illustrated and described the principles of the invention in several preferred embodiments, it should be apparent to those skilled in the art that the invention can be modified in arrangement and detail without departing from such principles. I claim all modifications coming within the spirit and scope of the following claims.

I claim:

1. A method for measuring amyloid degrading activity in serum or tissue, comprising the steps of:

forming a composition comprising a quantity of a dye bound to amyloid;

adding to the composition a quantity of serum or tissue homogenate, thereby forming a reaction mixture;

incubating the reaction mixture so that a portion of the composition reacts with amyloid degrading factors in the serum or tissue homogenate causing a portion of the amyloid to be degraded and the dye bound to the degraded amyloid portion to be released;

separating the reaction mixture into a portion of the composition that did not react with the amyloid degrading factors, a portion of degraded amyloid and a supernatant containing the dye released into the supernatant from the degraded amyloid portion;

spectrophotometrically measuring the quantity of the dye released into the supernatant; and calculating the quantity of the amyloid degraded based on the quantity of the dye released into the supernatant.

2. The method according to claim 1 wherein the dye is Congo red.

3. The method according to claim 2 wherein the amyloid is amyloid A.

4. The method according to claim 3 further comprising the step of suspending the composition in an aqueous buffered saline solution with a pH of from about 6.0 to about 10.0 before the step of adding to the composition a quantity of serum or tissue homogenate.

5. The method according to claim 4 further comprising the step of diluting the serum or tissue homogenate before the step of adding to the composition.

6. The method according to claim 5 wherein the step of incubating is carried out at a temperature of from about 30° C. to about 45° C.

7. The method according to claim 6 wherein the incubating is from about 20 minutes to about 60 minutes.

8. The method according to claim 7 further comprising adding an aqueous NaCl solution following the step of incubating and before the step of spectrophotometrically measuring.

9. The method according to claim 8 wherein the concentration of NaCl in the aqueous NaCl solution is from about 7% NaCl to about 11% NaCl.

10. The method according to claim 9 wherein the step of spectrophotometrically measuring is carried out with light at a wavelength in the range of from 450 nm to 550 nm.

11. A method for measuring amyloid A degrading activity in serum or tissue, comprising the steps of:

forming a substrate comprising a quantity of Congo red bound to amyloid A;

adding to the substrate a buffer solution, thereby forming a suspension;

adding to the suspension a quantity of serum or tissue homogenate, thereby forming a reaction mixture;

incubating the reaction mixture to form, by the action of amyloid degrading factors in the serum or tissue homogenate, reaction products comprising unreacted substrate, degraded amyloid A and a supernatant containing Congo red released into the supernatant from the degraded amyloid A;

separating the unreacted substrate and the supernatant;

spectrophotometrically measuring the quantity of Congo red released into the supernatant; and calculating the quantity of amyloid A degraded based on the quantity of Congo red released into the supernatant.

12. The method according to claim 11 wherein the buffer solution is a buffered saline solution with a pH of from about 6.0 to about 10.0.

13. The method according to claim 12 further comprising the step of diluting the serum or tissue homogenate before adding to the suspension.

14. The method according to claim 13 wherein the incubating is for from about 20 minutes to about 60 minutes.

15. The method according to claim 14 wherein the step of incubating is carried out at a temperature of from about 30° C. to about 45° C.

16. The method according to claim 15 further comprising adding an aqueous NaCl solution following the step of incubating.

17. The method according to claim 16 wherein the concentration of NaCl in the aqueous NaCl solution is from about 7% NaCl to about 11% NaCl.

18. The method according to claim 17 wherein the step of spectrophotometrically measuring is carried out with light at a wavelength in the range of from 450 nm to 550 nm.

19. A method for quantitatively measuring amyloid A degrading activity in serum or tissue, comprising the steps of:

forming a substrate comprising a quantity of Congo red bound to amyloid A;

adding to the substrate a buffer solution, thereby forming a suspension;

adding to the suspension a quantity of serum or tissue homogenate, thereby forming a reaction mixture;

incubating the reaction mixture to form reaction products comprising unreacted substrate, degraded amyloid A and a supernatant containing Congo red released into the supernatant from the degraded amyloid A;

adding to the reaction mixture a solution comprising NaCl and water;

separating the unreacted substrate and the supernatant;

spectrophotometrically measuring at about 505 nm the quantity of Congo red released into the supernatant; and calculating the quantity of amyloid A degraded based on the quantity of Congo red released into the supernatant.

20. A method for measuring amyloid degrading activity in serum or tissue, comprising the steps of:

forming a composition comprising a quantity of Congo red bound to an amyloid;

adding to the composition a quantity of serum or tissue homogenate, thereby forming a reaction mixture;

incubating the reaction mixture to allow amyloid degrading factors present in the serum or tissue homogenate to react with the amyloid component of the composition causing a portion of the amyloid to be degraded and the Congo red bound to the degraded amyloid portion to be released;

separating an unreacted portion of the composition and a supernatant containing the Congo red released into the supernatant from the degraded amyloid portion;

spectrophotometrically measuring the quantity of Congo red released into the supernatant; and calculating the quantity of the amyloid degraded based on the quantity of Congo red released into the supernatant.

* * * * *